United States Patent
Hacker (10) Patent No.: US 9,730,760 B2
(45) Date of Patent: Aug. 15, 2017

(54) ELECTROMAGNETIC RESONANT SURGICAL SCALPEL HANDLE AND ELECTROMAGNETIC SENSOR SYSTEM APPARATUS THEREOF

(71) Applicant: Steven M Hacker, Delray Beach, FL (US)

(72) Inventor: Steven M Hacker, Delray Beach, FL (US)

( * ) Notice: Subject to any disclaimer, the term of this patent is extended or adjusted under 35 U.S.C. 154(b) by 54 days.

(21) Appl. No.: 14/870,046

(22) Filed: Sep. 30, 2015

(65) Prior Publication Data

US 2017/0086925 A1    Mar. 30, 2017

(51) Int. Cl.
*G08B 1/08*        (2006.01)
*A61B 34/20*       (2016.01)
(Continued)

(52) U.S. Cl.
CPC .......... *A61B 34/20* (2016.02); *A61B 17/3211* (2013.01); *G01L 1/162* (2013.01);
(Continued)

(58) Field of Classification Search
CPC ................ A61B 34/20; A61B 17/3211; A61B 2034/2053; A61B 2090/065;
(Continued)

(56) References Cited

U.S. PATENT DOCUMENTS 6,347,460 B1 * 2/2002 Forrer .................... A61B 90/10
                                                       128/920
9,072,541 B2 * 7/2015 Hacker ............... A61B 17/3211
(Continued)

Primary Examiner — Joseph Feild
Assistant Examiner — Rufus Point
(74) Attorney, Agent, or Firm — Nancy J. Flint, Esq.

(57) ABSTRACT

A surgical scalpel handle with an internal chamber and a removable electromagnetic resonance signal generating cartridge and an electromagnetic resonance sensor system is disclosed. A surgical scalpel handle is provided for with an internal chamber comprised of two pieces, a front piece with a blade holder and a back piece and when attached, the front end section and the back end section together comprise an internal cavity. An electromagnetic resonance signal generating cartridge comprising one or more printed circuit boards (PCB) are in electrical contact upon which an application specific integrated circuit (ASIC) are mounted and having a magnet; a coil; and capacitor resonant circuit; an elastic member; a pressure sensitive feature; and having power source connections, and a removable power source having power source contacts; and power source connections complete the electrical contact between the electromagnetic signal generating cartridge and the removable power source housed in the internal cavity. An electromagnetic signal generating cartridge is disposed of in an internal cavity of a scalpel handle and generates an electromagnetic resonance signal. An electromagnetic sensor system apparatus with a sensor system disposed of vertical and horizontal planes is disclosed and is disposed of on a surgical table. The scalpel handle with an internal cavity and removable signal generating cartridge and with the electromagnetic sensor system apparatus with a sensor system can be used to digitally map the precise position, size, trajectory, shape, pressure and angle of the scalpel being used during surgical procedures. A pressure sensitive feature is disposed and in connection with the blade holder and the removable signal generating cartridge. The pressure exerted by a surgeon on the blade is transmitted through a blade holder to a pressure sensitive feature to switch from the stand by position of the cartridge to the on and generate an electromagnetic signal position. The emitted signals generated by the cartridge can be read by the provided for electromagnetic resonance sensor system to generate a digital record of coordinates in the x, y location in a horizontal plane and vertical plane as well as a digital record of trajectory of scalpel used during the procedure. The coordinates are stored in a memory device such as a RAM, tablet or computer. After commu-
(Continued)

nicating with a host machine, a monitor can display the surgeon's trace and exact location coordinates.

8 Claims, 8 Drawing Sheets

(51) Int. Cl.
*A61B 17/3211* (2006.01)
*G01L 1/16* (2006.01)
*A61B 17/00* (2006.01)
*A61B 90/00* (2016.01)

(52) U.S. Cl.
CPC ............... *A61B 2017/00075* (2013.01); *A61B 2017/00221* (2013.01); *A61B 2034/2053* (2016.02); *A61B 2090/065* (2016.02)

(58) Field of Classification Search
CPC .......... A61B 2017/00075; A61B 2017/00221; G01L 1/162
See application file for complete search history.

(56) References Cited

U.S. PATENT DOCUMENTS

| | | | |
|---|---|---|---|
| 2004/0102696 A1* | 5/2004 | Govari | A61B 5/06 600/424 |
| 2009/0253978 A1* | 10/2009 | Hashimshony | A61B 5/064 600/407 |
| 2014/0039517 A1* | 2/2014 | Bowling | B25J 13/00 606/130 |
| 2014/0323852 A1* | 10/2014 | Wald | A61B 5/062 600/424 |
| 2015/0119650 A1* | 4/2015 | Hacker | A61B 17/3211 600/249 |
| 2015/0150579 A1* | 6/2015 | Hacker | A61B 17/3211 606/167 |
| 2015/0351661 A1* | 12/2015 | Mezger | A61B 5/05 600/424 |
| 2016/0213430 A1* | 7/2016 | Mucha | A61B 5/062 |
| 2017/0086925 A1* | 3/2017 | Hacker | A61B 34/20 |

* cited by examiner

ELECTROMAGNETIC RESONANT SURGICAL SCALPEL HANDLE AND ELECTROMAGNETIC SENSOR SYSTEM APPARATUS THEREOF

FIELD OF THE INVENTION

The present invention relates to the field of surgical incision, excision and biopsy instruments. In particular, this invention relates to a surgical scalpel handle with an internal chamber and a removable electromagnetic resonance signal generating cartridge and an electromagnetic resonance sensor system allowing a surgeon to use a scalpel handle during surgery to digitally record and map the location, size, shape and trajectory of where a scalpel was used on a patient during surgical incisions, excisions or biopsies. A surgical scalpel handle is provided for with an internal chamber comprised of two pieces, a front piece with a blade holder and a back piece and when attached, the front end section and the back end section together comprise an internal cavity. An electromagnetic resonance signal generating cartridge comprising one or more printed circuit boards (PCB) are in electrical contact upon which an application specific integrated circuit (ASIC) are mounted and having a magnet; a coil; and capacitor resonant circuit; an elastic member; a pressure sensitive feature; and having power source connections, and a removable power source having power source contacts; and power source connections complete the electrical contact between the electromagnetic signal generating cartridge (EMSGC) and the removable power source are housed in the internal cavity. An electromagnetic signal generating cartridge is disposed of in an internal cavity of a scalpel handle and generates an electromagnetic resonance signal. An electromagnetic sensor system apparatus with a sensor system disposed of in vertical and horizontal planes is disclosed and is disposed of on a surgical table. The scalpel handle with an internal cavity and removable signal generating cartridge and with the electromagnetic sensor system apparatus with a sensor system can be used to digitally map the precise position, size, trajectory, shape, pressure and angle of the scalpel being used during surgical procedures. A pressure sensitive feature is disposed and in connection with the blade holder and the removable signal generating cartridge. The pressure exerted by a surgeon on the blade is transmitted through a blade holder to a pressure sensitive feature to switch from the stand by position of the cartridge to the on and generate an electromagnetic signal position. The emitted signals generated by the cartridge can be read by the provided for electromagnetic resonance sensor system to generate a digital record of coordinates in the x, y location in a horizontal plane and vertical plane as well as a digital record of trajectory of scalpel used during the procedure. The coordinates are stored in a memory device such as a RAM, tablet or computer. After communicating with a host machine, a monitor can display the surgeon's trace and exact location coordinates.

BACKGROUND OF THE INVENTION

Currently the most widely used computer input devices include the keyboard, mouse, digital pens, styluses, or a finger swipe on a digital tablet or phone. Due to advancement of digital technologies, more and more computer users are working with digitizer based devices such as a computer, tablet or phone that allow a user to write and draw upon the working area of the computer, tablet or phone and have the signals and codes interpreted by a computer. Specifically, the working area of such surfaces can detect and capture the position, pressure, and trajectory of such input devices. There are many such devices well known to the art U.S. Pat. Nos. 4,967,050, 6,999,067, 5,576,502, and 8,300,030 B2.

Also, well known to the art is a point detecting system for digitizers employing an electromagnetic signal utilizing system. This system comprises a sensor panel including a plurality of sensor coils arranged parallel to the detecting direction. The pointing device is provided with a coil or resonant circuit to perform electromagnetic interaction between the pointing device and the sensor coils. The sensor coils in the sensor panel transmit an electromagnetic wave and receive a response electromagnetic wave re-emitted by the interaction between the transmitted electromagnetic wave and the resonant circuit in the pointing device. The coordinate values of the pointing device are produced by arithmetic operation according to a main sensor signal generating the strongest electromagnetic energy and supplemental sensor signals adjacent to the main sensor as described in Japanese Patent Publication No. 2-53805/1990 and Japanese Patent Application Open Publication No. 3-147012/1991.

Other well-known systems include a sensor panel that transmits an electromagnetic wave and a pointing device that receives the signal and then the reverse, a pointing device transmits an electromagnetic wave and a sensor plate receives the transmitted signal. In these systems, electromagnetic mutual functions are utilized and the pointing device includes a coil or resonant circuit. Furthermore, theses pointing devices have a pressure sensing function to sense device pressure, and have an on off switching mechanism to input switching information at a required position. This is accomplished by changing the resonant condition from the norm position of the coil or resonant circuit. This is disclosed in U.S. Pat. Nos. 5,576,502, 8,947,405 B2 and Japanese Patent Application Open Publications No 63-257823/1988, No 64-53223/1989, No 4-96212/1992 and No. 5-275283/1993.

Also, well known to the art is the active induction method of using an electromagnetic stylus to generate an electromagnetic signal. The active induction method involves installing a power source into the electromagnetic stylus to provide the electromagnetic stylus with sufficient electrical energy for emitting electromagnetic signals. Accordingly the electromagnetic stylus can actively emit the signals to an X/Y axis antenna array on a digital panel for position. This is disclosed in U.S. Pat. Nos. 8,947,405 B2 and 8,300,030 B2.

Also well known to the art is a typical electromagnetic induction type of tablet that may comprise a two-dimensional loop antenna array, multiplexers, analog signal amplifiers, band pass filters, rectifiers, integrator, peak-sampling circuit, analog-to-digital circuit, frequency counting circuit, microprocessor, and the like as disclosed in U.S. Pat. Nos. 7,005,843 and 8,300,030 B2.

Also, the precise position of a digital pen's tracing on a digital tablet can be recorded using a variety of techniques other than electromagnetic resonance and are also well known to the art and include the following: Resistive technology whereby mapping of the pens location is achieved through a resistive sensor sandwiched between two conductive coated plastic films. Pressure on the surface of the plastic films causes electrical resistance to change and allows for the determination of location and pressure intensity by determining the variation in the distance between the two plastic layers. Capacitive technology uses a capacitive sensor that measures the difference in capacitance when a stylus presses on the surface of a capacitive touch screen. Optical technology utilizes a pen and touch technology that utilizes infra-red light as the input method and through the use of mirrors and light sources around the edge of a screen, so that when the stylus object breaks the plane of infra red light, optical sensors recognize this dark sport and that data is used to provide input data. The above constructions however, are severely limited for use during surgery in that the sensor screen cannot be reproduced in the surgical suite and require the pen to touch the tablet surface.

Also, well known to the art, Physicians and surgeons attach a blade to a universal bayonet that is attached to a scalpel handle to cut human tissue for a variety of purposes. When a surgeons uses a scalpel, it is well known to the art that a surgeon or their assistant at the time of surgery, manually measure and record the location of the surgery by using anatomic landmarks on the body and a traditional metric ruler to convey the location in their medical record or to another physician to complete treatment. Also, a surgeon will approximate or manually measure the trajectory and describe the shape of the trajectory and manually add that to the medical record. There are significant limitations to this prior art in that the measurements are often forgotten to be performed, or are often approximated, incomplete, unreliable, arbitrary or often wrong, making the record of the procedure unreliable and challenging for future care by other surgeons, physicians and challenging for medical documentation purposes including billing and medico legal purposes.

The ability to digitally map the precise coordinates while a surgeon deploys a scalpel handle to perform surgical procedures such as excisions, incisions and biopsies on a patient and the ability to digitally map the size, shape and trajectory form of a scalpel used during a surgical procedure on a body is challenging for a surgeon. Currently, the surgeon, if not forgotten at the time of surgery, manually measures with a traditional ruler and manually records in the patient record the approximate distances from anatomic landmarks on the body to document where a surgical procedure took place on the body. A surgeon typically uses a traditional metric ruler to approximate and measure the size and shape of surgical excision, incision or biopsy.

There are limitations in the prior art for using electromagnetic resonance mapping of a surgical procedure as it occurs and to insure that a surgeon's measurements are precise, reliable, reproducible and recorded digitally with digital coordinates at the time of the surgical procedure, and similarly there are limitations in the prior art to record or reliably reproduce precise mapping of location, size and shape of procedures related to the body and related to surgical procedures, incision, excision or biopsies.

There are limitations of the prior art regarding the use of an operating room or surgical table sensor system that enables electromagnetic resonance signals to digitally record or map precisely the coordinate location and trajectory form where a surgeon used his scalpel to perform surgical incisions, excisions or biopsies.

Additional limitations of prior art regarding the use of a magnetic resonance generating scalpel handle in use with a electromagnetic resonance sensor system that enables a surgeon to convert his hand held approach and hand held directed surgical trajectory into a digital on line form.

Additional limitations of prior art regarding a surgeon's limitation to being able to digitally map coordinates of his surgical position and surgical trajectory on a patient during surgery using a scalpel handle.

Additional limitations of prior art utilizing capacitance or resistance technologies for mapping techniques are limited for their use of a scalpel on a body during surgery by the requirement of touching or approximating a digital tablet, computer or phone as a sensor board with a stylus or finger swipe . . . .

Additional limitations of prior art of manually measuring or approximating surgical procedure locations and trajectories as performed by a surgeon are that the measurements are not reproducible, often unreliable, and imprecise and performed after that fact, and require manual input into a digital medical record and therefore subject to human error and misinterpretation with no standardization.

Accordingly, a methodology, which overcomes the shortcomings of prior art, is desired.

SUMMARY OF THE INVENTION

In accordance with the present invention, a surgical scalpel handle with an internal chamber and a removable electromagnetic resonance signal generating cartridge and an electromagnetic resonance sensor system allowing a surgeon to use a scalpel handle during surgery to digitally map and record the location, size, shape and trajectory of where a scalpel was used during a surgical procedure on a patient during surgical incisions, excisions or biopsies.

In one embodiment, the invention comprises a surgical scalpel handle with internal chamber comprised of two pieces, a front piece with a blade holder and a back piece with a power source contact; a removable electromagnetic resonant signal generating cartridge comprised of a power source; a printed circuit board (PCB); an application specific integrated circuit (ASIC); a magnet; a coil; a capacitor resonant circuit; an elastic member; and a pressure sensitive feature; such that when enclosed within the chamber of the assembled scalpel handle it comprises a scalpel handle that is in the stand by position and ready to generate a electromagnetic resonance signal position. A pressure sensitive feature is provided for in the electromagnetic resonant signal generating cartridge and in connection with a blade holder and upon cutting, pressure is detected by the pressure sensitive feature and turns on electromagnetic resonant signal generating cartridge to generate an electromagnetic resonance signal position.

In one embodiment, the invention comprises a scalpel handle that is able to generate a electromagnetic resonance signal, that when used in the presence of an electromagnetic sensor system, a scalpel handle can be used to digitally map the coordinate position, size, trajectory, shape, pressure and angle of the scalpel when being used during surgical procedures.

In one embodiment, the invention comprises a removable signal generating cartridge that remains in the incomplete and power off position and requires that the surgical scalpel handle pieces are assembled to switch to a stand by power on position and such assembly completes the circuit on the signal generating cartridge, such that the back piece of the surgical scalpel handle contains a contact for a power sources as contained within the removable signal generating cartridge; and such that the removable signal generating cartridge fits into the chamber of the front end and back end of the handle In one embodiment, the invention comprises a signal switch mechanism whereby the pressure exerted by the surgeon on the blade upon cutting is transmitted through the blade holder to the pressure sensitive feature through a series of piezoelectric sheets to switch the cartridge from a stand by on position to cause the cartridge to generate a electromagnetic signal.

In one embodiment, the invention comprises a electromagnetic resonance sensor system that generates a digital record of location with x and y coordinates in horizontal and vertical planes and scalpel trajectory forms with x and y coordinates in horizontal and vertical axis.

In one embodiment, the invention comprises a system whereby the coordinates are stored in a memory device such as a RAM, tablet or computer.

In one embodiment, the invention comprises a system whereby after communicating digital data with a host machine, a monitor can display the surgeon's trace and exact location in a two and three dimensional displays.

In one embodiment, the invention comprises a electromagnetic resonance signal generating technology to send electromagnetic waves from an electromagnetic sensor system that resides on top of or inside a surgical table and receives and sends electromagnetic resonance modes in a regular interval of microseconds with an electromagnetic induction device.

In one embodiment, the invention comprises a electromagnetic signal emitted from the electromagnetic sensor system stimulates oscillation in the coil and capacitor resonant circuit in the signal-generating cartridge contained in the chamber of a scalpel handle.

In one embodiment, the invention comprises a resonant circuit contained in a signal-generating cartridge enclosed in a chamber of a scalpel handle generates an electromagnetic signal that is received by a sensor system comprised of a plurality of sensor coils arranged in parallel and perpendicular to the detecting direction. The sensor coils in the sensor system transmit an electromagnetic wave and receive a response electromagnetic wave re-emitted by the interaction between the transmitted electromagnetic wave and a resonant circuit in the signal-generating cartridge enclosed in the chamber of the scalpel handle.

In one embodiment, the invention comprises a scalpel handle that generates coordinate values that are produced by arithmetic operation according to a main sensor signal generating the strongest electromagnetic energy and supplemental sensor signals adjacent to the main sensor and may be displayed in two dimensions or three dimensions.

In one embodiment, the invention comprises a signal-generating cartridge and a pressure sensitive feature including a series of piezoelectric sheets that communicate with a blade holder attached to the front end of a scalpel handle.

In one embodiment, the invention comprises a signal-generating cartridge enclosed in a chamber of a scalpel handle has a unique ID that is sent back to a sensor system, which sends a signal back to a resonant circuit in a signal-generating cartridge.

In one embodiment, the invention comprises a sensor system composed of a flat surface and two perpendicular surfaces at each end of the flat surface such that a grid of wires in the x and y axis are disposed of on the flat horizontal surface and a separate grid of wires are placed in an x and y axis and disposed of in the vertical planes such that vertical planes are disposed of perpendicularly at the both ends of a flat horizontal surface.

In one embodiment, the invention comprises a electromagnetic sensor system is composed of a flat surface and two perpendicular surfaces at each end of the flat surface and is disposed of on top of or inside of a surgical table.

In one embodiment, the invention comprises a sensor system generates a close-coupled electromagnetic field known as a B-Field and that this close coupled electromagnetic field stimulates oscillation in a signal generating cartridge's coil and a circuit enclosed in a chamber of scalpel handle.

In one embodiment, the invention comprises a sensor system is composed of a long flat surface and two perpendicular surfaces at each end of the flat surface such that the system can be disposed of on or inside of a surgical table and a patient can lie on top of flat surface where a patient's head rests against the perpendicular surface at one end and the patient's feet rests against the perpendicular surface at the other end.

In one embodiment, the invention comprises a sensor system is composed of a long flat surface and two perpendicular surfaces at each end of the flat surface such that the system can be placed on top of or inside of a surgical table and consists of a typical electromagnetic induction sensor system with a loop antenna array, analog signal amplifiers, band pass filters, rectifiers, integrator, peak sampling circuit, analog to digital circuit, frequency counting circuit and microprocessor.

In one embodiment, the invention comprises an electromagnetic sensor is in the receive mode, the energy is reflected back to the grid of wires, and communicate to a modulator and chip contained in the sensor system and which distributes the digital information and data to a computer such that the information provided to and analyzed by the computer is used to determine the scalpel handle's position by interpolation and Fourier analysis of the signal intensity.

In one embodiment, the invention comprises a signal generating cartridge contained within the scalpel handle to communicate other vital information to the sensor system and the computer to include such data as pressure sensitivity, scalpel handle and blade orientation and signal generating cartridge unique ID.

In one embodiment, the invention comprises an electromagnetic scalpel handle which generates an electromagnetic signal which can be received by a sensor system without direct contact to a sensor system and the signal-generating cartridge can emit a electromagnetic signal with a special frequency continuously, with the intensity of the signal maintained.

In one embodiment, the invention comprises a sensor system consisting of a grid of wires generating an electromagnetic resonance signal, sensor board and control board consisting of a film in which a large number of overlapping loop (antenna) coils are arranged in a matrix in the x and y axis directions underneath the patient parallel with the surgical table, and then a separate sensor system perpendicular to the table at the headboard and footboard consisting of a grid of wires generating an electromagnetic resonance signal, sensor board and control board consisting of a film in which a large number of overlapping loop (antenna) coils are arranged in a matrix in the x and y axis directions.

In one embodiment, the invention comprises an under-surface of a sensor board that is a shield board installed to block out noise from other components such as the motherboard or nearby circuits.

In one embodiment, the invention comprises a control board which discharges alternating current to the select loop coils from among the array installed on the sensor board. This excites the coils, causing them to generate magnetic fields. When the scalpel passes through these magnetic fields, it picks up and stores energy in its resonant circuit. A control board first detects a scalpel handle's rough location by scanning the loop coils on a sensor board. Then, it scans multiple loop coils in the vicinity of a scalpel handle and uses the information to calculate a scalpel handle's coordinate value precisely.

In one embodiment, the invention comprises a scalpel handle which can be a short distance from a sensor surface and that this distance can be amplified through a variety of measures including increasing the transmitting coil size to increase efficiency of the system.

In one embodiment, the invention comprises a low priced computer with powerful microchips can be used to perform the digital signal processing.

In one embodiment, the invention comprises a surgical scalpel handle with a front piece and a rear piece and with an internal chamber to house an electromagnetic resonant signal generating removable cartridge is assembled with an electromagnetic resonant signal generating removable cartridge inserted before assembly.

In one embodiment, the invention comprises a the front portion of a scalpel handle and the rear portion of a scalpel handle containing a contact for a removable power source provided for in an internal chamber to house an electromagnetic resonant signal generating removable cartridge are disassembled. In one embodiment, the removable power source comprises a battery. In one embodiment, the removable power source comprises a rechargeable battery. In one embodiment, the removable power source comprises a plurality of batteries connected in series. In one embodiment, the removable power source comprises a AAAA or AAA battery.

In one embodiment, the invention comprises a surgical scalpel handle assembled and described herein is made of disposable material it may be disposed of in its entirety with the blade attached and the signal-generating cartridge contained within it. If the surgical handle is assembled described herein is made of non-disposable material, than as is commonly done in the art, the blade will be removed from the bayonet fitting of the blade holder and the surgical scalpel handle is disassembled to separate the front end piece from the back end piece, so that the enclosed electromagnetic signal generating cartridge may be removed from the internal chamber of both pieces and then both front end and back end pieces of the surgical scalpel handle may properly sterilized prior to next use. If the surgical handle is made of disposable material and the enclosed electromagnetic signal generating cartridge is made of non-disposable material, than as is commonly done in the art, the blade will remain attached to the blade holder and the surgical scalpel handle is disassembled to separate the front end piece from the back end piece, so that the enclosed electromagnetic signal generating cartridge may be removed from the internal chamber and reused for another surgery and both front end and back end pieces of the surgical scalpel handle will be disposed of in its entirety.

In one embodiment, the invention comprises an electromagnetic sensor system disposed of on top of or inside of a table such that an electromagnetic sensor system is covered by either a cushion or drape of a surgical table as is common in the art and such that the electromagnetic sensor system cannot be directly contacted or contaminated by the patient's body when patient is placed atop of a electromagnetic sensor system and such that the electromagnetic system is reusable and does not require sterilization.

In one embodiment, the invention comprises an electromagnetic sensor system disposed of on top of or inside of a table and may be switched to the on position such that when used with a scalpel handle with an electromagnetic resonant signal generating removable cartridge a digital map of the location and trajectory form of the scalpel handle as used by the surgeon may be recorded While this invention has been particularly shown and described in reference to the preferred embodiments thereof, it would be understood by those skilled in the art that various changes in form and detail may be made therein without departing from the scope and spirit of the invention encompassed by the impended claims. Although the embodiments have been described in reference to a scalpel handle with a removable, electromagnetic signal generating cartridge and an electromagnetic sensor system apparatus thereof. It is the object of the invention that prior to surgery, the present invention may also apply to any surgical instrument or device, or any medical device, that would require digital mapping and trajectory form mapping during a surgical procedure in order that a device may be used on or in the body for treating, excising, incising or diagnosing including but not limited to surgical laser instruments, endoscopes, curettes, surgical wire instruments, scalpels, and other surgical instruments. Numerous modifications, changes, variations, substitution and equivalents will be apparent to those skilled in the art without departing from the spirit and scope of the invention as described in the claims.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

The various features of the present invention and the manner of attaining them will be described in greater detail with reference to the following description, claims, drawings, wherein reference numerals are reused, where appropriate to indicate a correspondence between the referenced items, and wherein the preferred embodiments of the invention will herein after be described in conjunction with appended drawings to illustrate and not to limit the invention wherein like designations denote like elements and in which:

DETAILED DESCRIPTION OF THE PREFERRED EMBODIMENT

Figure 1:
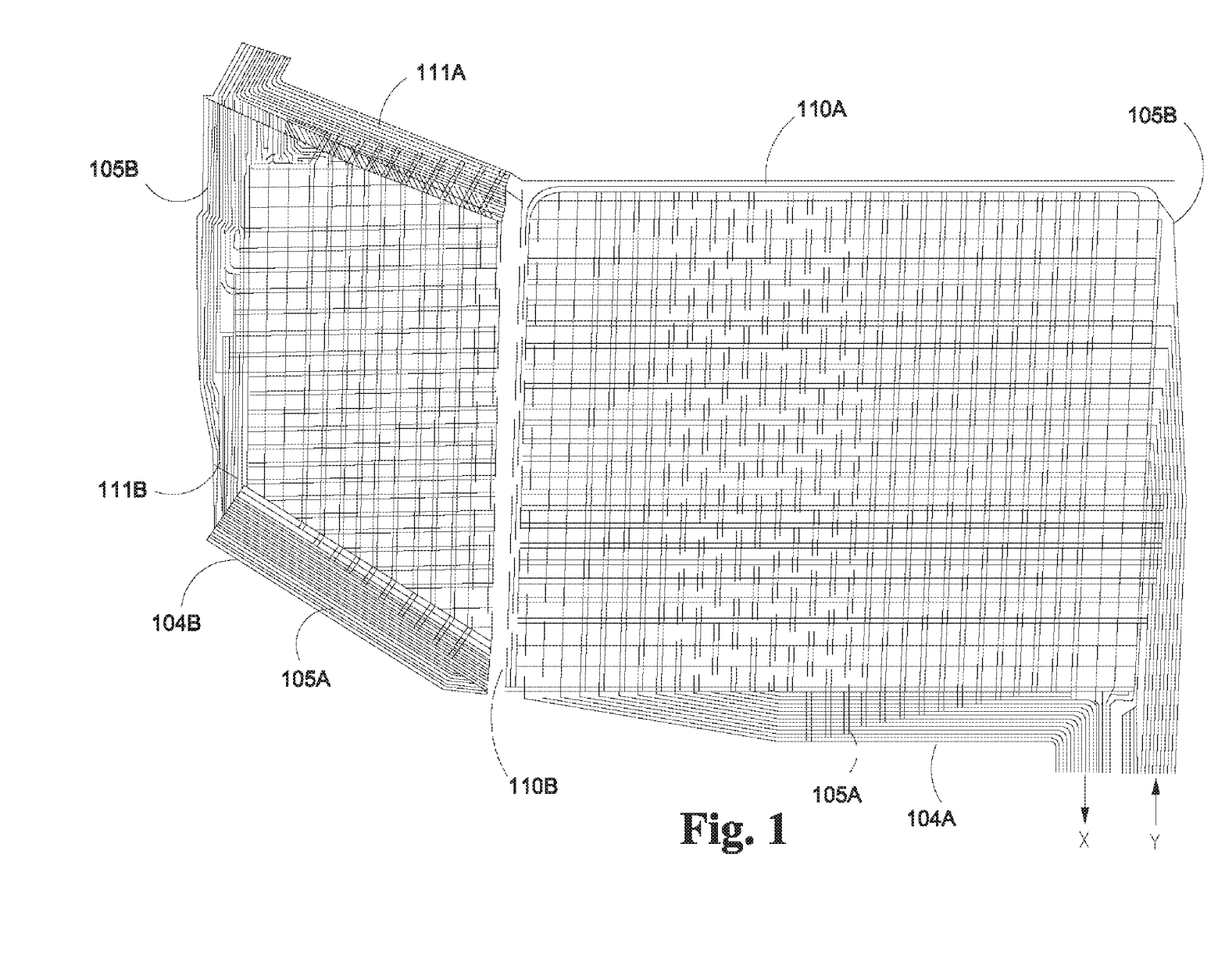
FIG. 1 shows a conventional arrangement of loop antenna arrays disposed of perpendicularly in horizontal and vertical planes.

FIG. 1, shows the electromagnetic sensor system with the antenna array arrangements disposed in which an x coordinate antenna array 110A and a y coordinate antenna array 110 B in horizontal plane 104A and a separate x coordinate antenna array 111A and a separate y coordinate antenna array in 111B are disposed of in vertical plan 104B and are respectively connected to a ground line 105A and a ground line 105B and an x-coordinate antenna array 110A and a y-coordinate array 110B and an x coordinate antenna array 111A and a y coordinate antenna array in 111B cross through the ground line 105a and 105B respectively, for forming a plurality of loop wires and hence the electromagnetic sensor system may be disposed of on top of or inside of a surgical table.

Figure 2:
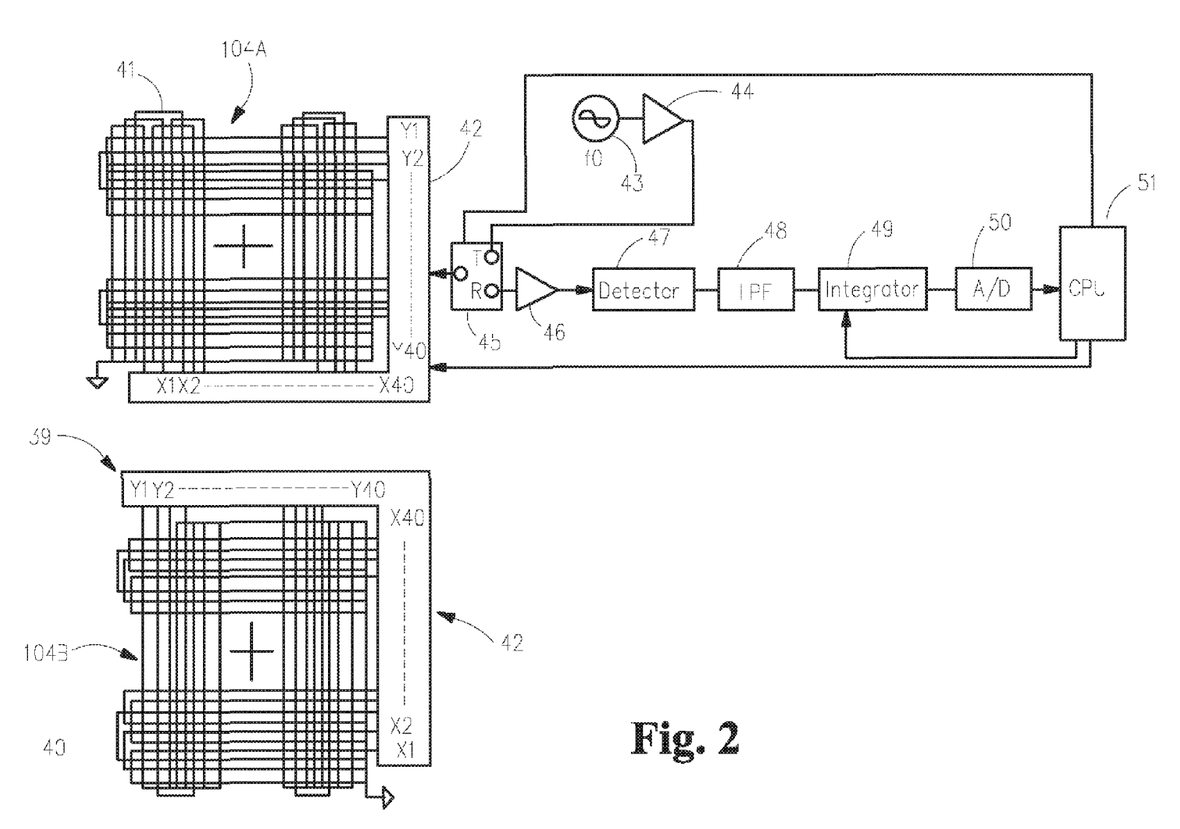
FIG. 2 is an block diagram of a conventional electromagnetic induction sensor layout revealing both horizontal and vertical planes.

FIG. 2, shows a sensor system as previously described by U.S. Pat. No. 7,005,843. Note a loop coil group 41 arranged as x1 to x40 and y1 to y40, in an x axis direction and y axis direction respectively in horizontal plane 104A and a loop coil group 40 arranged as x1 to x40 and y1 to y40, in an x axis direction and y axis direction respectively in vertical plane 104B. These loop coils are connected to a selection circuit 42 for selecting each of the loop coils in the horizontal plane 104A and selection circuit 39 in the vertical plane 104B. An oscillation circuit 43 disposed of in the removable electromagnetic resonance generating cartridge of a scalpel handle (not shown) oscillates at a resonant frequency, which is the same frequency as frequency f0 of electromagnetic waves transmitted from sensor system. The resonant circuit 43 is connected to the transmissions side (T) of a transmission/reception switching circuit 42 and 39 and electromagnetic waves at the frequency f0 are emitted from the selected loop coil to the removable electromagnetic resonance-generating cartridge of a scalpel handle. The reception side (R) of the transmission reception switching circuit 45 is connected to an amplifying circuit 46 which is connected to a detector circuit 47. The detector circuit 47 is connected to a low pass filter (LPF) 48, which is connected to an integration amplifier 49, and stores and holds reception signals for a specified time. The voltage held by the integration amplifier 49 is outputted to an A/D conversion circuit 50, the out put of which is connected to a CPU (central processing unit) 51.

The electromagnetic resonance sensor system disposed on top of or inside of a surgical table, employs a double side amplitude method that is using the maximum detection voltage and another two detection voltages obtained from the left side and the right side of the antennas that senses the maximum detection voltage, to determine the coordinate of the removable electromagnetic resonance generating cartridge of a scalpel handle. The loop antenna array must be arranged under the whole surface area including the edge.

Figure 3:
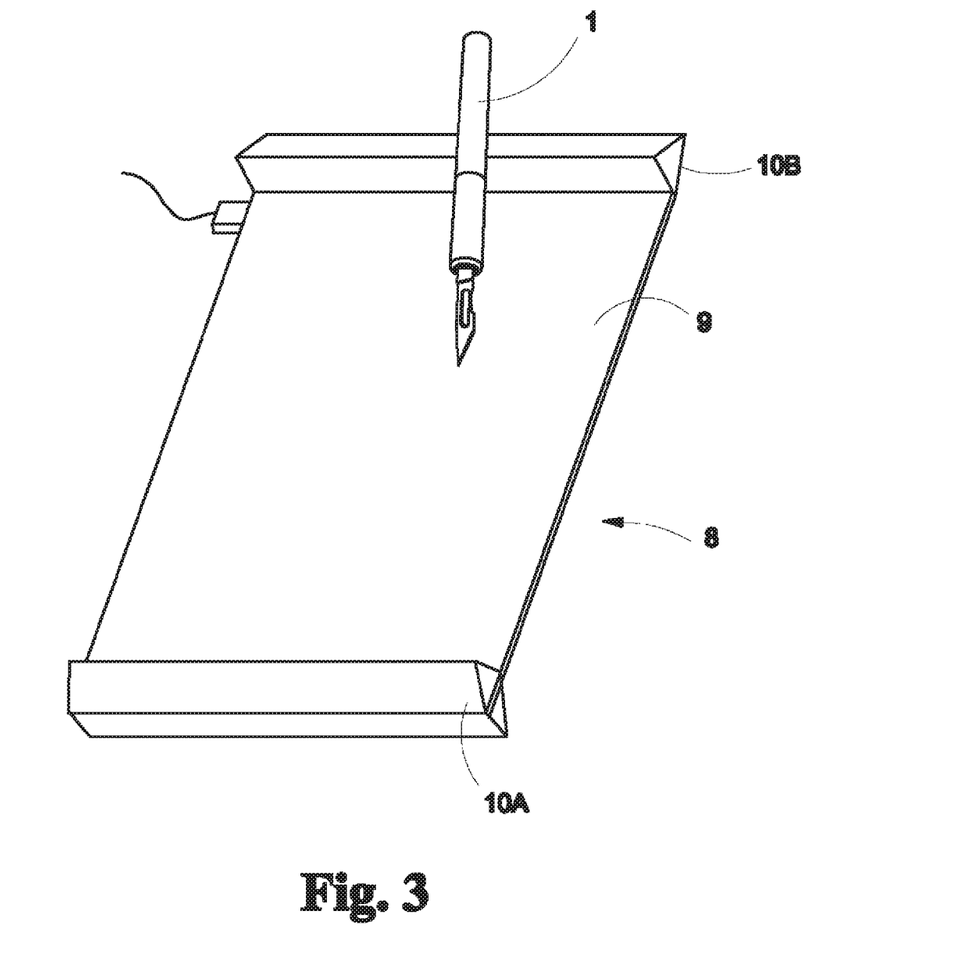
FIG. 3 shows an embodiment of electromagnetic sensor system according to present invention.

FIG. 3, shows the electromagnetic resonance sensor system 8 according to one embodiment of present invention. A scalpel handle 1 is employed for inputting of the electromagnetic resonance signals that are received by the electromagnetic resonance sensor system 8. The electromagnetic sensor system 8 comprises a horizontal area 9 and a vertical areas 10A and 10B disposed of perpendicularly at both ends of horizontal area 9. An x-y axis loop antenna array is arranged in both the horizontal area 9 and the vertical areas 10A and 10B. In the present invention the electromagnetic resonance sensor system is equivalent to a "digitizer" or other kinds of similar products. The user holds the scalpel handle 1 to perform surgery on the patient lying within and on top of the areas defined by horizontal area 9 and vertical areas 10A and 10B in aggregate the entire electromagnetic resonance sensor system 8.

Figure 4:
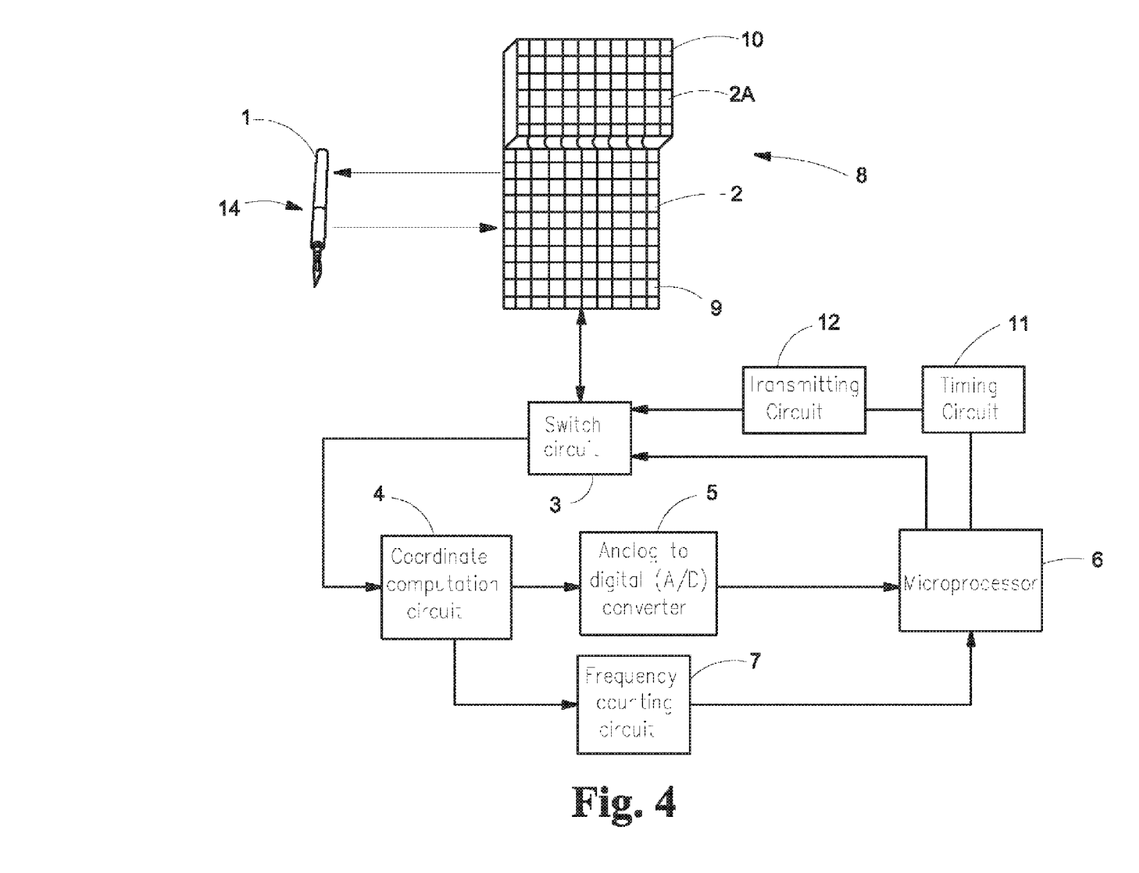
FIG. 4 shows a block diagram of the electromagnetic sensor system according to present invention.

FIG. 4 shows a block diagram of the electromagnetic sensor system 8 according to one embodiment of the present invention. An x-y loop antenna array 2 disposed in horizontal area 9 and a x-y loop axis loop antenna array 2a disposed in vertical area 10 and is arranged inside sensor system 8. The electromagnetic resonance sensor system 8 further comprises a switch circuit 3, a coordinate computation circuit 4, an analog to digital converter 5, a microprocessor 6, a timing circuit 11, a transmitting circuit 12, and a frequency counting circuit 7. The electromagnetic sensor system 8 may comprise other components and the above mentioned components may comprise filters, amplifiers, rectifiers, or other components.

By switching the switch circuit 3, the microprocessor 6 instructs specific antennas of the x-y loop antenna array 2 and 2a to detect electromagnetic wave radiated from the scalpel handle 1. The computed coordinates are then transmitted to A/D converter 5 to convert to digital values. The microprocessor 6 processes the digital coordinate values and controls the activities of the other components.

The scalpel handle 1 contains a removable electromagnetic resonance signal-generating cartridge 14. A signal-generating cartridge comprises an oscillating circuit consisting of inductors and capacitors (LC). The sensor system 8 radiates an electromagnetic wave having frequency that is the same frequency off the oscillating circuit, causing a frequency resonance with the oscillating circuit and the inductance of the oscillating circuit will be changed and the frequency of the oscillating circuit is varied. The greater is the pressure of the scalpel handle 1 exerted as determined by the pressure sensitive feature, the greater is the inductance of the oscillating circuit. The greater is the inductance of the oscillating circuit, the greater is the variance of the frequency of the oscillating circuit. Therefore, the variation of the pressure exerted can be estimated by checking the variation of the frequency of the oscillating circuit. The frequency counting circuit 7 counts the frequency of the electromagnetic waves received by the coordinate computation circuit 4 and the counter results are transmitted to the microprocessor 6, therefore the variation of the pressure exerted can be estimated by the microprocessor 6.

The x-y loop antenna arrays 2 and 2a may be arranged inside the sensor system 8 in a double-faced, arrayed and equidistant manner. The x-y loop antenna arrays 2 and 2a array 11 senses electromagnetic waves radiated from the electromagnetic resonance signal generating cartridge 14 disposed of in the scalpel handle 1. By switching the switch circuit 3, the microprocessor 6 instructs specific antennas of x-y loop antenna arrays 2 and 2a to detect electromagnetic wave radiated from the scalpel handle 1' to the nearest antenna and will sense the maximum voltage. The coordinate computation circuit 4 comprises a plurality of registers for storing voltage obtained from the antennas. The sequential voltages will be employed for computing the coordinate of the electromagnetic resonance signal-generating cartridge 14 disposed of in the scalpel handle 1.

Figure 5:
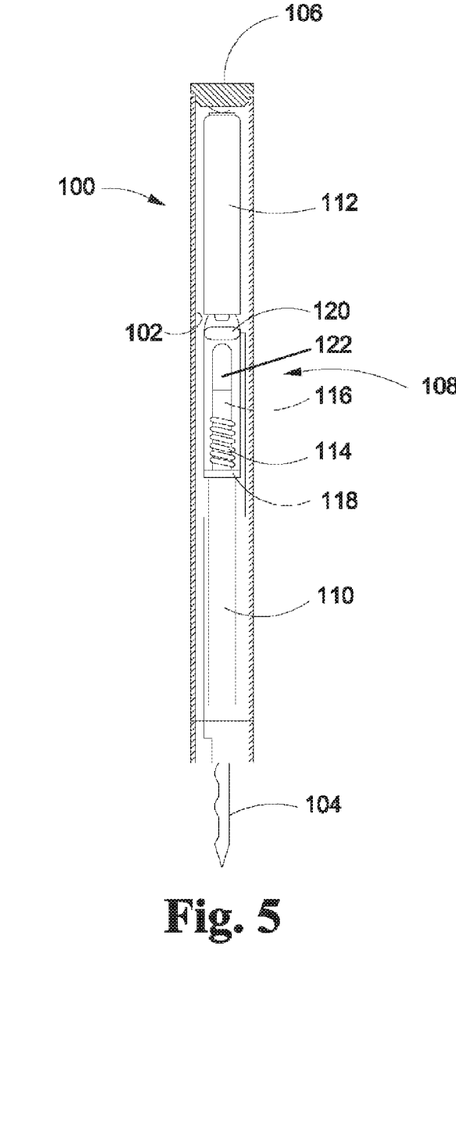
FIG. 5 is a perspective view of a removable, re-usable signal generating electromagnetic resonance cartridge in accordance with the present invention.

FIG. 5 shows a diagram of an signal generating electromagnetic resonance cartridge 100 according to the present invention. The electromagnetic resonance cartridge 100 includes a hollow body 103, a pressure sensitive feature, 104, a cap 106, an energy transforming device 108, a circuit board 110, and an power source 112. The hollow body 102 is depicted for clearly displaying the inner components of electromagnetic resonance cartridge 100. The pressure sensitive feature 104 and the cap 106 are disposed on two ends of the hollow body 102 respectively for containing the inner components (energy transforming device 108, the circuit board 110, and the power source 112) of the electromagnetic resonance cartridge 100 cooperatively with the hollow body 102. The circuit board 110 is disposed in the hollow body 102 and electrically connected to the energy-transforming device 108. The circuit board 110 is used for rectifying the electrical signals transformed by the energy-transforming device 108, and thereby converting alternative currents generated from the energy transforming device 108 into direct currents. The power source 112 is disposed in the hollow body 102 and is connected electrically to the pressure sensitive feature 104 and the circuit board 110. The power source 112 is used for receiving the electrical signals from the circuit board 110 to general electrical energy and providing the electrical energy to the pressure sensitive feature 104 to generate electromagnetic signals. The power source 112 can be a capacitance device.

The energy-transforming device 108 is used for transforming dynamic energy into the electrical signals. The energy-transforming device includes a coil 114, a magnet 116, first piezoelectric sheets 118 and a second piezoelectric sheet 120. The coil 114 is electrically connected to the circuit board 110.

Figure 6:
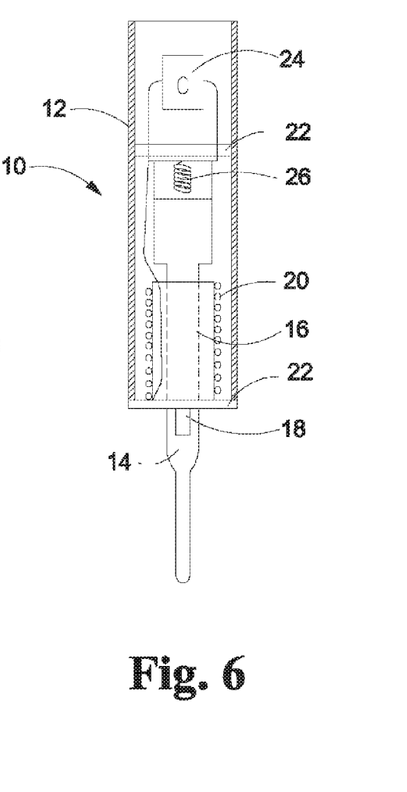
FIG. 6 is a diagram of a conventional electromagnetic resonance inductance system contained in a scalpel handle in accordance of the present invention.

FIG. 6 (U.S. Pat. No. 5,576,501 FIG. 1) shows a resonant circuit and an energy transforming device within the signal generating electromagnetic resonance cartridge 10 where the coil 20 and the power source or capacitance device 24 constitute a resonant circuit. The resonance conditions for this resonant circuit are determined so as to make resonance with the electromagnetic wave transmitted to and received from sensor coils. The external casing 12 of the electronic resonance cartridge formed in a cylindrical shape, a pressure sensitive feature arranged on the axis of the external casing 12, a core support member 16 composed of a ferrite core with a movable magnetic member 18 and an elastic member or coil spring 26. Inductance of the coil 20 depends on the distance between the ferrite core 16 and the movable magnetic member 18. The piezoelectric sheet 22 is disposed of at the top and bottom of the resonant circuit and communicates with pressure sensitive feature 14. The elastic member 26 may be a coil spring or an elastic rubber may be used.

Figure 7:
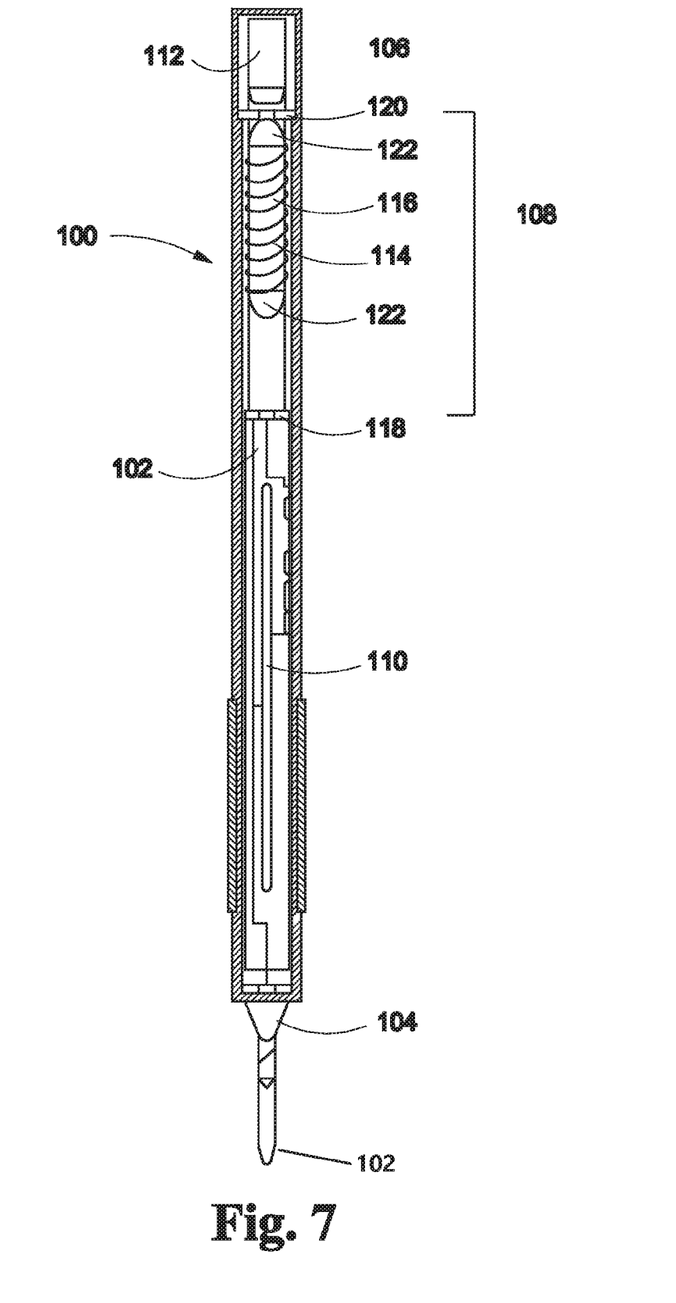
FIG. 7 is a sectional diagram of electromagnetic signal-generating cartridge in accordance of the present invention.

FIG. 7 is a sectional diagram of the scalpel handle 100. The energy-transforming device 108 is disposed of in the hollow body 102. The energy-transforming device 108 includes a coil 114, a magnet 116, a first piezoelectric sheet 118 and a second piezoelectric sheet 120. The. Coil 114 is electrically connected to the circuit board 110. The magnet is 116 movably disposed in the coil 114 for moving back and forth relative to the coil 114 to make the coil 114 generate the electrical signals. The first piezoelectric sheet 118 and the second piezoelectric sheet 120 are made of piezoelectric material. When the material receives an external stress such as from pressure received by the pressure sensitive feature 104 connected to blade holder of scalpel handle 102, polarization may occur within and then an electric field or electric displacement may be generated accordingly between two conductive surfaces of the piezoelectric material. As a result, the surface of the piezoelectric material may generate the electrical signals and can be used for receiving the impact of the magnet to generate the electrical signals. There may be disposed a buffer member 122 of any material such as rubber or spring with a buffer function such that when the magnet 116 hits the first piezoelectric sheet 118 and the second piezoelectric sheet 120, the trauma of such impact is minimized to not damage the system. The buffer member 22 also can provide the magnet 116 with some elastic force to move back and forth so that the energy generating efficiency of the energy-transforming device 108 is increased accordingly. The electrical signals are sent to the circuit board 110 continuously. After the circuit board 110 rectifies the received electrical signals, the electrical signals generated by the coil 114, the first piezoelectric sheet 118 and the second piezoelectric sheet 120 can be converted from alternative current signals into direct current signals and transmitted to the power source 112 to generate the electrical energy.

Figure 8A:
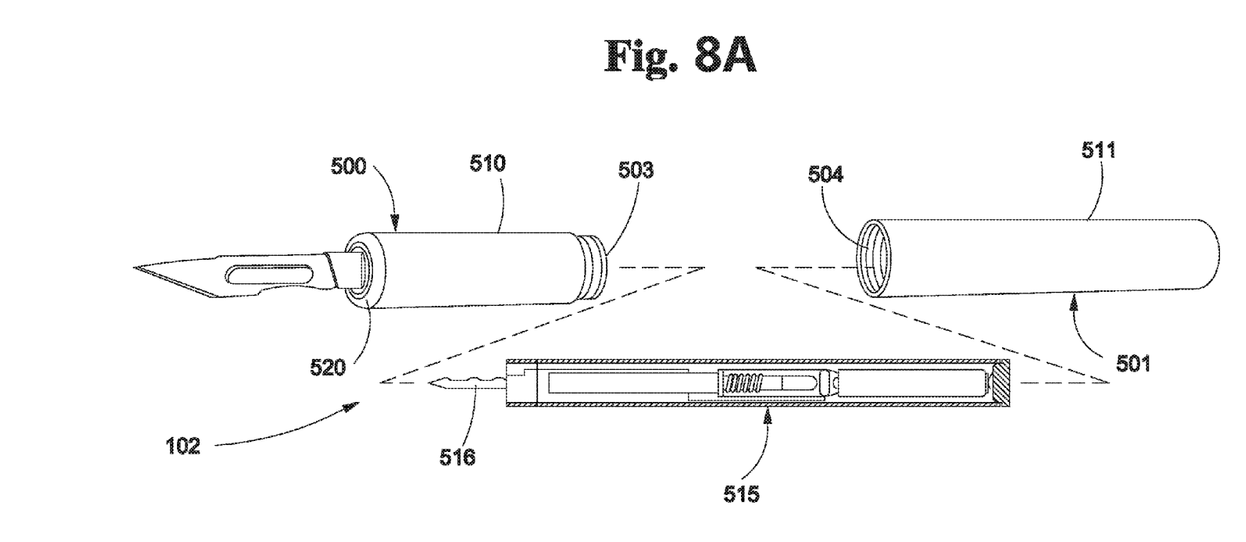
FIG. 8A is an embodiment of the scalpel handle in the disassembled state which includes two sections, a front end section of handle with blade holder attachment and a rear back end of handle with contact for a power source in accordance of the present invention.
Figure 8B:
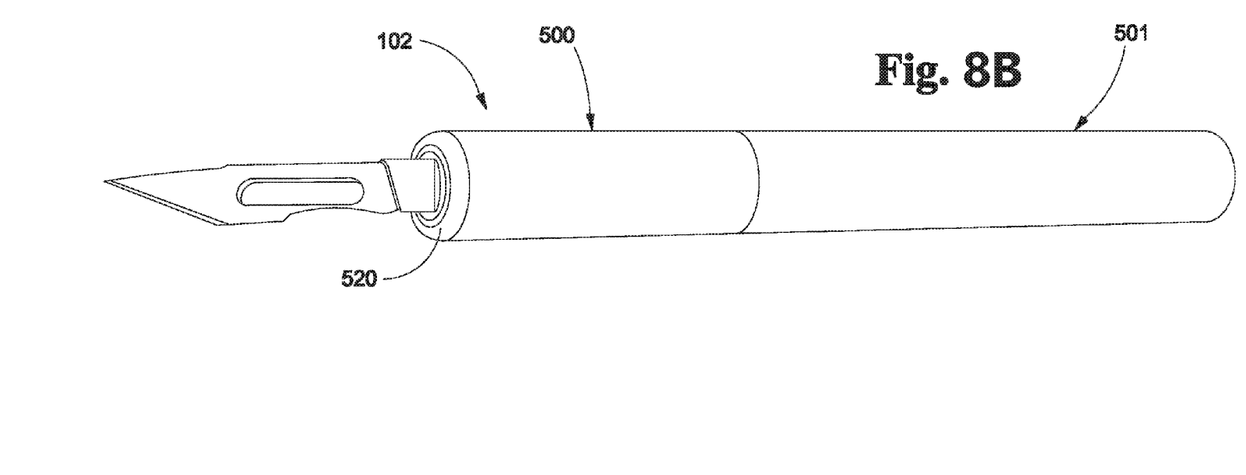
FIG. 8B is an embodiment of the scalpel handle in the assembled state which includes two sections, a front end section of handle with blade holder attachment and a rear back end of handle in accordance of the present invention.

Refer to FIGS. 8A and 8B, FIG. 8A refers to the scalpel handle 102 in the dissembled state and FIG. 8B shows the scalpel handle 102 in the assembled state ready to cut configuration, and hereinafter, a "front end" 500 represents the distal portion of scalpel handle closest to the blade holder 520 and includes the blade holder attachment and a "rear or back end" 501 represents the back end or proximal half of handle, which includes a contact (not shown) to complete circuit of power source and power signal generating cartridge. The scalpel handle 500 and 501 has an external casing 510 and 511 formed in a cylindrical hollow member made of material that will not block transmitting and receiving of electromagnetic material. The external casing 510 and 511 is designed to have a similar shape to commonly used scalpel handles such as round scalpel handles and the like from the view point of the user or surgeon's handling facility. Therefore the casing 510 and 511 has a tapered forward end with a front opening 511 through which a blade holder 520 protrudes. The external casing 510 and 511 further contains a male thread 503 on casing 510 and a female thread 504 on casing 511 such that when both casings 510 and 511 are twisted together in accordance with male and female threads the circuit is completed and the signal generating cartridge 515 is in the stand by and ready to generate electromagnetic resonance position. The capacitance of the variable capacitor of the resonant circuit contained within the signal generating cartridge 515 will be varied in response to scalpel pressures as determined by pressure sensitive feature 516 that communicates with blade holder 520 and such that a change of this resonant state will represent an on and "generating signal" operation.

Figure 9A:
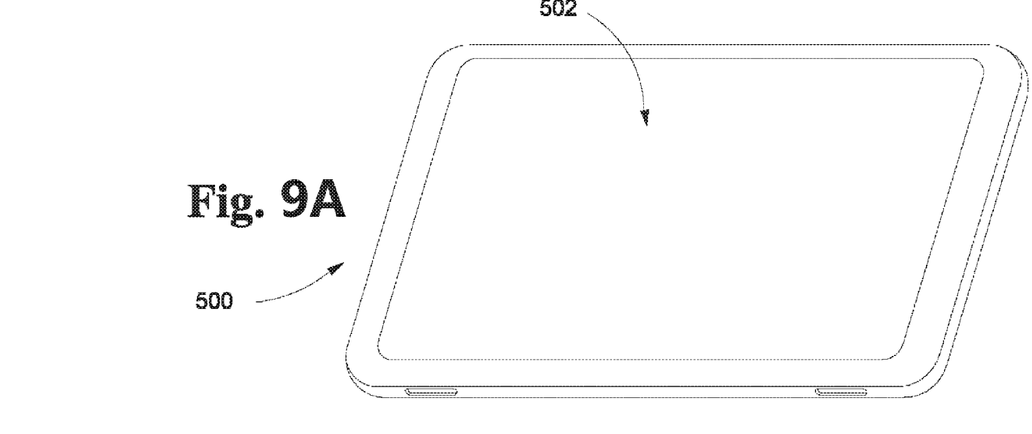
FIG. 9A is a diagram of a computer apparatus in one embodiment of the present invention.
Figure 9B:
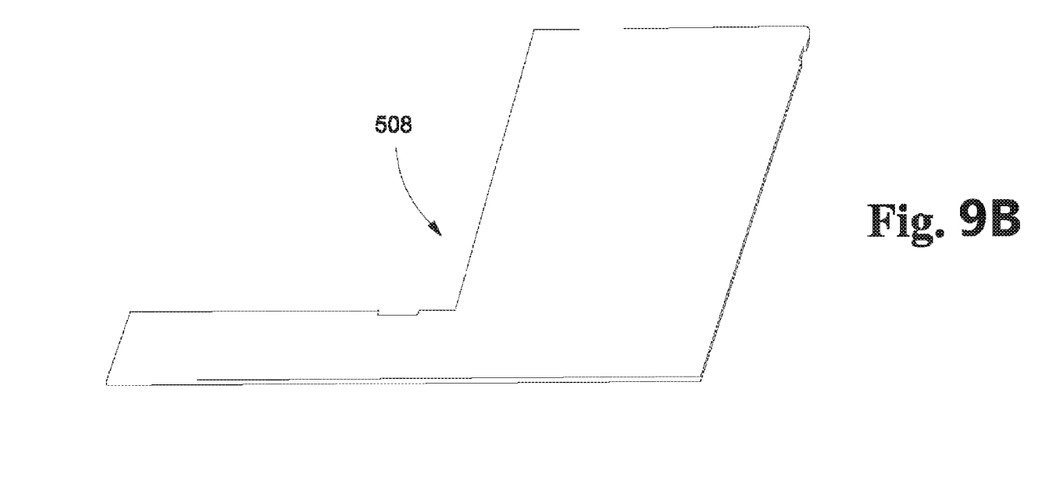
FIG. 9B is a diagram of host device typically disposed of on undersurface of computer apparatus in one embodiment of the present invention.

FIG. 9A shows a diagram of a computer apparatus 500 and includes a computer module 502. The computer module 502 can be a conventional desktop computer or portable computer (e.g. notebook or laptop). The computer module 502 is depicted as a notebook in FIG. 8A. The computer module 502 includes a host device 508 typically disposed of on undersurface of computer apparatus 500 as depicted in FIG. 9B. The host device 508 can include common components installed in a computer, such as a motherboard and a central processing unit (CPU). The related descriptions are omitted herein since it is commonly seen in the prior art.

What is claimed as new and desired to be protected by Letters Patent of the United States is:

1. A digital coordinate mapping and trajectory form mapping surgical sensor system comprising:
a scalpel handle comprising an electromagnetic resonant circuit and induction device, wherein the electromagnetic resonant circuit and induction device comprises a removable electromagnetic resonance signal-generating cartridge, wherein the removable electromagnetic resonance signal-generating cartridge comprises an oscillating circuit, the oscillating circuit comprising a plurality of inductors and capacitors, wherein the oscillating circuit radiates an electromagnetic wave having a frequency changeable according to its inductance, wherein the oscillating circuit emits an electromagnetic wave having an initial frequency prior to changing of its inductance; and a surgical platform area comprising a horizontal plane defined by an x-y loop antenna array arranged to form an x-y coordinate system and two vertical planes each defined by defined by an x-y loop antenna array arranged to form an x-y coordinate system, each x-y loop antenna array comprising a first loop coil group disposed in the x direction of the x-y coordinate system and a second loop coil group disposed in the y direction of the x-y coordinate system, each first and second loop coil group comprising a plurality of antennas, one of the two vertical planes disposed at opposite ends of the horizontal plane, the surgical platform area further comprising:
a switch circuit;
a coordinate computation circuit comprising a plurality of amplifiers to receive detection voltages from the plurality of antennas in each first and second loop coil group to compute a coordinate of the scalpel handle;
an analog to digital converter;
a microprocessor; and
a frequency counting circuit, wherein the frequency counting circuit counts the frequency of the electromagnetic waves received by the coordinated computation circuit, and the surgical platform area emits an electromagnetic wave having the same frequency as the initial electromagnetic wave emitted by the oscillating circuit,
wherein each x-y loop antenna array, the switch circuit, the coordinate computation circuit, the analog to digital converter and the frequency counting circuit are in communication with and under control of the microprocessor,
wherein electromagnetic waves emitted by the removable electromagnetic resonance signal-generating cartridge of the scalpel handle are altered from the original frequency under of a user of the scalpel handle, the electromagnetic wave frequency being changeable according to pressure placed on a pressure sensitive feature of the scalpel handle by the user of the scalpel handle,
wherein the emitted electromagnetic waves are detected by one or more antennas in the first and second loop coil arrays,
wherein upon receipt of a signal from the switch circuit the microprocessor instructs the antennas to sense the maximum voltage of the emitted electromagnetic waves,
wherein the sensed maximum voltages of the emitted electromagnetic waves are stored in one or more registers in the coordinate computation circuit,
wherein the x-y coordinates of the antennas that detect the emitted electromagnetic waves are transmitted to the analog to digital converter where the x-y coordinates are converted to digital values,
wherein the microprocessor estimates variation of pressure placed on the scalpel handle according to the variation of the frequency of the emitted electromagnetic waves from the initial electromagnetic wave frequency, and
wherein the position, trajectory, shape, pressure and angle of the scalpel handle is determined to coordinate with the location of the emitted electromagnetic waves of the removable electromagnetic resonance signal-generating cartridge as detected by the antennas comprising the x-y loop antenna arrays.

2. The digital coordinate mapping and trajectory form mapping surgical sensor system of claim 1, wherein the scalpel handle further comprises:
a front portion and a rear portion, the front portion and back portion defining a hollow interior cavity, the front portion comprising a scalpel blade holder and the rear portion comprising a power source contact;
a pressure sensitive feature in contact with a blade disposed in the scalpel blade holder that detects a force in relation to pressure on a blade attached to the front portion of the scalpel handle;
a printed circuit board;
a power source in contact with the pressure sensitive feature and the printed circuit board; and
an energy transforming device for generating power in contact with the printed circuit board.

3. The digital coordinate mapping and trajectory form mapping surgical sensor system of claim 2, wherein the energy transforming device comprises two piezoelectric sheets disposed on either end of the coil, wherein movement of the magnet within the coil impacts the piezoelectric sheets causing generation of electric signals, wherein the electric signals are transmitted to the circuit board where they are rectified from alternative current signals to direct current signals and thereafter transmitted to the power source.

4. The digital coordinate mapping and trajectory form mapping surgical sensor system of claim 2, wherein the power source comprises a capacitance device.

5. The digital coordinate mapping and trajectory form mapping surgical sensor system of claim 2, wherein the energy transforming device comprises a coil, a magnet and first and second piezoelectric sheets, wherein the coil is electrically connected to the printed circuit board.

6. The digital coordinate mapping and trajectory form mapping surgical sensor system of claim 1, wherein position, trajectory, shape, pressure and angle of the scalpel handle coordinates with the scalpel handle's use of the scalpel handle during a surgical procedure, wherein a patient is disposed in the surgical platform area.

7. The digital coordinate mapping and trajectory form mapping surgical sensor system of claim 6, wherein the surgical procedure comprises excision, incision or biopsy.

8. The digital coordinate mapping and trajectory form mapping surgical sensor system of claim 2, wherein the pressure sensitive feature turns on power to the removable electromagnetic resonance signal-generating cartridge causing it to generate an electromagnetic wave in response to the amount of force of the pressure placed on the blade.

* * * * *